United States Patent [19]

Harris et al.

[11] 4,218,379
[45] Aug. 19, 1980

[54] PROCESS FOR THE PRODUCTION OF MACROCYCLIC ESTERS

[75] Inventors: Eugene G. Harris, West Chester, Ohio; John F. White, Princeton, N.J.

[73] Assignee: Emery Industries, Inc., Cincinnati, Ohio

[21] Appl. No.: 970,617

[22] Filed: Dec. 18, 1978

Related U.S. Application Data

[63] Continuation-in-part of Ser. No. 835,253, Sep. 21, 1977, Pat. No. 4,165,321.

[51] Int. Cl.² .................. C07D 323/00; C07D 327/00; C07D 321/00; C07D 313/00
[52] U.S. Cl. .................................. 260/340.2; 549/10; 549/11; 260/343
[58] Field of Search ............... 260/340.2, 343; 549/10, 549/11

[56] References Cited

U.S. PATENT DOCUMENTS 4,105,672  8/1978  Rueter et al. .................... 260/340.2

OTHER PUBLICATIONS

Chemical Abstracts, vol. 78 (1973) 158966q; 158968s.
Chemical Abstracts, vol. 79 (1973) 6158k.

*Primary Examiner*—Norma S. Milestone
*Attorney, Agent, or Firm*—Kenneth D. Tremain

[57] ABSTRACT

A process is provided for the continuous or semi-continuous production of hetero-macrocyclic compounds including lactones and cyclic esters. The process involves the catalyzed depolymerization of linear polyesters at elevated temperature and under reduced pressure in the presence of a specified amount of monocarboxylate moieties while providing top-to-bottom mixing throughout essentially the total volume of the reaction mass.

12 Claims, No Drawings

PROCESS FOR THE PRODUCTION OF MACROCYCLIC ESTERS

CROSS-REFERENCES

This is a continuation-in-part of our copending application Ser. No. 835,253, filed Sept. 21, 1977, now U.S. Pat. No. 4,165,321.

BACKGROUND OF THE INVENTION

Since the principle odor constituents of natural musks are macrocyclic compounds, numerous synthetic methods have been devised for the preparation of various macrocycles in an attempt to duplicate the natural musk odor. The method most commonly used for the preparation of lactones, ether-lactones and cyclic esters is the depolymerization of the corresponding linear polyester accompanied by ring closure. For example, lactones are obtained by depolymerizing the high molecular weight product obtained from the condensation of hydroxy acids, e.g. 15-hydroxypentadecanoic acid. Similarly, macrocyclic esters result when polyesters obtained by the condensation of dicarboxylic acids and diols are depolymerized.

Depolymerization procedures are described in U.S. Pat. No. 2,092,031, Czech Pat. No. 108,762 and the article by E. W. Spanagel and W. H. Carothers in J. Amer. Chem. Soc., Vol. 57, 929-934 (1935). In a typical process of this type, the polyester is heated at an elevated temperature, but below the temperature of thermal decomposition, in the presence of an inorganic catalyst. The catalyst is generally a chloride, nitrate, carbonate, borate, oxide, hydroxide or organic acid salt of a divalent metal such as magnesium, manganese, iron, cobalt, lead or tin. The depolymerization is carried out under reduced pressure and the macrocyclic compound and other volatile products formed during the course of the reaction removed from the reaction vessel.

While depolymerization procedures are presently considered to be the best and therefore preferred method for synthesizing macrocyclic lactones, ether-lactones and esters, such processes are not without certain disadvantages. The principle difficulty with depolymerization processes of this type is the viscosity of the reaction mass. The linear polyesters are themselves highly viscous materials by virtue of their high molecular weight but during the depolymerization reaction the viscosity is even further increased so than an intractable plastic mass is formed due to chain-growth reactions occurring between partially depolymerized fragments present in the reaction mass. It is not uncommon, even during the very early stages od depolymerization, for the reaction mass to become so viscous that agitation by conventional means is not possible. Heat transfer within such highly viscous, virtually solid reaction masses is very poor resulting in a highly inefficient reaction, namely, a slow rate of depolymerization and the formation of large amounts of undesirable byproducts.

As a result of the viscosity/heat transfer problems associated with these reactions, long reaction times are required even when using the most effective catalysts and reduced pressure and it is not feasible to carry out these reactions on a large scale and obtain acceptable yields of the desired macrocyclic compounds. Accordingly, it has not heretofore been possible to carry out these depolymerizations as anything but batch-type operations, thereby severely limiting the practical utility of such processes for commercial purposes. Even with batch-type operations it has been necessary to conduct the reaction of a relatively small scale and unless very elaborate process equipment designed to maximize heat transfer is used, it is possible to operate at only a fraction of the total reactor capacity to avoid destructive thermal decomposition, excessive foaming and other related problems. It would be highly advantageous therefore, if depolymerization processes could be conducted on a larger scale while minimizing the viscosity/heat transfer problems. It would be even more desirable if the depolymerization could be conducted as a continuous or semi-continuous operation and if high yields of the macrocyclic compounds were possible.

SUMMARY OF THE INVENTION

We have now quite unexpectedly discovered an improved process for the production of hetero-macrocyclic compounds, including lactones, ether-lactones, cyclic esters and cyclic ether-esters, by the depolymerization of the corresponding linear polyesters. By this process it is possible to prepare macrocyclic compounds of good quality and minimize the formation of undesirable byproducts. Also, this process overcomes many of the disadvantages associated with previously known reactions resulting from poor heat transfer and the high viscosity of the reaction mass thereby making it possible to conduct this process on a larger scale than was heretofore possible if acceptable conversions were to be obtained. Additionally, the process of this invention can be conducted as a continuous or semi-continuous operation.

To achieve the aforementioned improved results, the depolymerization process of this invention is conducted at an elevated temperature and reduced pressure with a metal catalyst using agitation which provides top-to-bottom mixing throughout essentially the total volume of the reaction mixture and in the presence of at least 0.75 mole percent of monocarboxylate. The monocarboxylate moieties can be introduced into the system with the catalyst, with the polyester being depolymerized or by the addition of a suitable ester to the reactor. The monocarboxylate moieties can be derived from either aliphatic or aromatic monocarboxylic acids containing from about 6 to 40 carbon atoms, and more preferably 10 to 30 carbon atoms, and will be present in the range 1.25 to 5.0 mole percent. Top-to-bottom mixing throughout the reaction mass is achieved by the use of inverted multiple-blade conical vessels wherein the blades have a helical configuration and are arranged to rotate throughout essentially the entire reaction mass and in close proximity to the interior surface of the reactor and in a direction which provides downward flow within the reaction mixture. Particularly advantageous are reactors formed by two inverted intersecting vertical cones and having two conical helical ribbon blades which fit the inner contour of the bowl formed by the cones and whose axes coincide with the axes of the cones and which intermesh as they rotate in opposite directions at the same speed.

Temperatures, pressures and catalysts used for the present improved process can be varied. Reaction temperatures can range from 200° C. to 400° C. but preferably will be between 250° C. and 350° C. The pressure will typically be less than 50 mm Hg and more usually be between 0.1 mm Hg and 10 mm Hg. From 0.1 to 10 weight percent of a metal oxide, hydroxide, halide or carboxylate of an organic acid is employed to catalyze the depolymerization. While it is possible to employ compounds of numerous metals for this purpose, magnesium, titanium, manganese, iron, cobalt, tin and lead compounds are preferred, particularly when present in the range 0.1 to 5 weight percent.

DETAILED DESCRIPTION

The improved process of this invention is adaptable for the preparation of a wide variety of heterocyclic macrocyclic compounds. It is particularly useful for the preparation of cyclic esters, cyclic ether-esters, lactones and ether-lactones having 8 to 20 atoms in the ring.

Hetero-macrocyclic compounds obtained by this process correspond to the general formulae

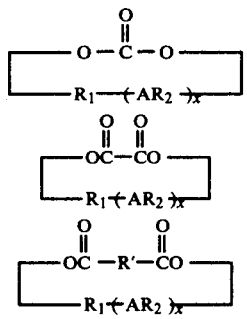

wherein R' is a bivalent hydrocarbon radical, which can be branched or straight chain, saturated or contain unsaturation, having 1 to 15 carbon atoms, $R_1$ is a saturated bivalent hydrocarbon radical having 1 to 17 carbon atoms, $R_2$ is a saturated bivalent hydrocarbon radical having 1 to 8 carbon atoms, A is a radical selected from the group —O—, —S—, —NH— and —NR*—, where R* is a $C_{1-4}$ alkyl group, and x is an integer from 0 to 4, and

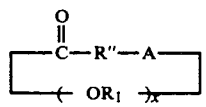

where R" is a bivalent hydrocarbon radical, branched or straight chain, saturated or unsaturated having 1 to 18 carbon atoms, and $R_1$ and x are the same as defined above and A is the same as defined above except that when x is zero A can only be oxygen.

The present improved process is especially useful for the production of macrocyclic esters corresponding to the formula

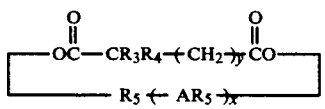

wherein $R_3$ and $R_4$ are hydrogen or a $C_{1-4}$ alkyl group, $R_5$ is a saturated bivalent hydrocarbon radical having 2 to 13 carbon atoms, y is an integer from 0 to 11 and A and x are the same as defined above. It is even more advantageous for the preparation of cyclic ester and ether-ester compounds of the general formula

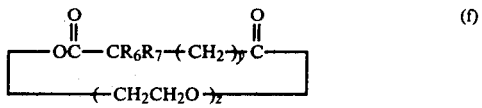

wherein $R_6$ and $R_7$ are hydrogen, methyl or ethyl groups, z is an integer from 1 to 4 and y is the same as defined above. Especially preferred macrocyclic compounds useful as odorants in applications where fragrance chemicals are used and corresponding to the formula

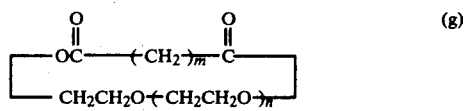

where m is an integer from 4 to 11 and n is 0 or 1 are prepared by the process of this invention and obtained in good yield and purity.

Illustrative macrocyclic esters and ether-esters which can be obtained using the depolymerization process of this invention include: tetradecamethylene carbonate, dodecamethylene oxalate, 7-thia-tridecamethylene oxalate, 7-oxa-tridecamethylene oxalate, dodecamethylene malonate, decamethylene malonate, ethylene suberate, ethylene azelate, 3-thia-pentamethylene azelate, 3-oxa-pentamethylene azelate, 3-methylpentamethylene sebacate, ethylene undecanedioate, ethylene dodecanedioate, methylene dodecanedioate, methylene brassylate, ethylidine brassylate, ethylene brassylate, ethylene-α-methylbrassylate, ethylene-α,α-dimethylbrassylate, ethylene-α-ethylbrassylate, and the like. In addition to the aforementioned products still other products including bicyclic and polycyclic materials such as hexamethylene cis (or trans)-tetra (or hexa) hydrophthalate can be obtained by the process of this invention.

More preferably the lactones obtained by the process of this invention will correspond to the formula

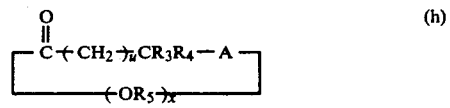

wherein u is an integer from 5 to 14, $R_3$, $R_4$, $R_5$ and x are the same as defined above and A is the same as defined above except that when x is zero A can only be oxygen. Even more preferred lactones and ether-lactones of the formula

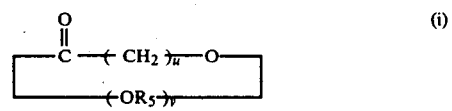

where v is 0, 1, or 2, $R_5$ and u are the same as defined above are obtained by the present improved process. Exemplary lactones and ether-lactones corresponding to the above formulae include: pentadecanolide, hexadecanolide, 10-oxa-hexadecanolide, 10-thia-pentadecanolide, 11-oxa-hexadecanolide, 11-thia-pentadecanolide, 12-oxa-hexadecanolide and 12-thia-pentadecanolide.

To obtain the macrocyclic compound the corresponding linear polyester is depolymerized in accordance with the procedure which will be described more fully below. For example, to obtain the cyclic ester corresponding to the formula (f) the polyester to be depolymerized will have repeating units of the formula

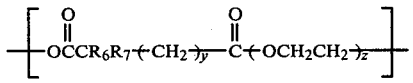

where, $R_6$, $R_7$, y and z are the same as already defined. The terminal groups of the polyester are not critical and may be hydroxyl or hydrogen groups or, as will be more fully explained below, it may be advantageous to have the polyester capped with a monocarboxylic acid. Excellent results are obtained using polyesters which have a hydroxyl value. The preparation of the linear polyester is not critical and plays no part in the present invention. The polyester is obtained using conventional condensation polymerization techniques known to the art. Generally, essentially equimolar amounts of the dicarboxylic acids and glycols, such as ethyleneglycol, diethyleneglycol or the like, are heated at an elevated temperature at reduced pressure for several hours. A catalyst may be employed which can be particularly effective during the latter stages of the polymerization. If desired, a monocarboxylic acid may be included to serve as a terminator. The linear polyesters, depending on their molecular weight and reactants from which they are formed, can range from highly viscous liquids to solid waxy masses. Similarly to obtain lactones, polyesters obtained by the condensation of hydroxy-substituted monocarboxylic acids are employed. For the formation of ether-lactones, a polyester obtained by the condensation of a hydroxy acid containing an ether linkage is depolymerized.

The above-described macrocyclic compounds are conveniently obtained in high yields and good purity from the improved process of this invention which in general terms involves the catalyzed depolymerization of a linear polyester at an elevated temperature and under reduced pressure in the presence of monocarboxylate moieties and with agitation which provides top-to-bottom mixing throughout the total volume of the reaction mass. The temperature at which the depolymerization is conducted can be in the range of 200° C. to 400° C. but is necessarily below the thermal decomposition temperature of the polyester and macrocyclic compound. More generally, the reaction temperature will range from about 250° C. to about 350° C. In addition to the elevated temperature the depolymerization is conducted under reduced pressure, typically less than about 50 mm Hg and, more preferably, at a pressure less than about 10 mm Hg and to as low as 0.01 mm Hg. The temperature and pressure employed will vary depending on the particular polyester to be depolymerized and to a large extent will be governed by the design of the process equipment.

The depolymerization process is conducted in the presence of from about 0.01 to 10% by weight, based on the polyester, of a metal catalyst. Numerous metal catalysts have been described in the prior art and can be used for the process of this invention. In general, Lewis acid metallic salts of Group IIIa, IVa, IVb, Va, VIIb and VIII metals (periodic Table of the Elements, Handbook of Chemistry and Physics, 57th Ed., CRC Press, Inc.) such as the oxides, hydroxides, halides or carboxylates of these metals are employed to catalyze the depolymerization. Especially helpful in the process of this invention are the oxides, hydroxides, chlorides and carboxylates of organic acids having from 2 to 30 carbon atoms of magnesium, titanium, manganese, iron, cobalt, tin and lead. Lead and tin compounds are particularly advantageous. Products having low residual metal contents are obtained using lead carboxylates of organic acids having from 8 to 22 carbon atoms. Best results are obtained when about 0.1 to about 5 weight percent of the catalyst is used.

The catalyst may be present in the polyester or fed to the reactor as such, in which case it may be charged at the outset of the reaction or added continuously or incrementally during the course of the depolymerization process. Since the catalyst can be combined with the polyester prior to depolymerization, it is possible to employ the same metal compound as catalyst for the preparation of the polyester and as the depolymerization catalyst, or if different catalysts are employed, the depolymerization catalyst can be added to the polyester during the final stage or at the end of the condensation reaction. Suitable catalysts for the depolymerization process include but are not limited to lead (II) oxide, red lead, lead (II) oxalate, lead (II) stearate, lead (II) palmitate, lead (II) coconoates, cobalt (II) chloride, tin (II) oxide, tin (IV) oxide, tin (II) chloride, tin (II) oxalate, tin (II) stearate, iron (III) chloride, antimony (II) chloride, magnesium oxide, magnesium chloride hexahydrate, manganese (II) chloride tetrahydrate, cobalt (II) chloride hexahydrate, iron (II) chloride tetrahydrate, n-butyl stannoic acid, di-n-butyl tin diacetate, condensed butyl titanate, and the like.

It has now quite unexpectedly been discovered that when the depolymerization is conducted using the above-defined temperatures, pressures and catalysts and in the presence of a specified amount of monocarboxylate moieties and with agitation which provides top-to-bottom mixing throughout essentially the total volume of the reaction mass, highly unexpected results are obtained. In accordance with the process of this invention it is possible to conduct the depolymerization as a continuous or semi-continuous process while obtaining products of good quality in high yield.

The monocarboxylate

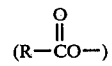

moieties can result from any one of several sources or a combination thereof, so long as the concentration of the monocarboxylate is at least 0.75 mole percent. The source of the monocarboxylate may be the catalyst, such as when a metal monocarboxylate catalyst is employed, or they can be introduced into the reaction system as the terminating group of the polyester to be depolymerized, such as when the polyester is capped with a monocarboxylic acid. Also, the monocarboxylic may be introduced into the system by the addition of a suitable ester, such as ethylene distearate, during the depolymerization. The concentration of the monocarboxylate moieties can range as high as 10 mole percent and in some cases even higher, however, practical and economic considerations dictate that the monocarboxylate concentration be kept as low as possible. Preferably the monocarboxylate will range between 1.25-5.0 mole percent. If the concentration of monocarboxylate is too high excessive amounts of solid residues will be formed. Also, the possibility that esters of these monocarboxylates will be carried over with the macrocyclic compounds during the distillation is increased thereby making purification of the resulting macrocyclic compound more difficult.

The monocarboxylate moieties are derived from monocarboxylic acids, aliphatic or aromatic, containing from about 6 to 40 carbon atoms. Whey they are obtained from aliphatic monocarboxylic acids they preferably will contain from about 10 to 30 carbon atoms. Both straight-chain and branched-chain fatty acids are useful. Monocarboxylates where the radical R is a cycloalkyl moiety can also be employed for the process of this invention. Excellent results are obtained where mixed aliphatic monocarboxylates derived from a mixture of fatty acids having varying chain lengths typically between about 10 to 30 carbon atoms are used. Preferably the aromatic moieties are derived from acids having from about 7 to 30 carbon atoms. The aromatic moiety can be phenyl, naphthyl or other polynuclear aromatic moieties, which can contain one or more substituents such as $C_{1-20}$ alkyl; $C_{3-8}$ cycloalkyl; $C_{1-20}$ alkoxy; halo, primarily chloro and bromo; or similar groups which will not interfere with the depolymerization and are thermally stable at the process temperatures. The carboxyl group may be directly substituted on the aromatic ring or linked thereto through a bivalent aliphatic hydrocarbon radical having from 1 up to about 12 carbon atoms. Exemplary aromatic acids of the above types and useful for the purpose of this invention include: benzoic acid, naphthoic acid, p-methoxybenzoic acid, p-isopropoxybenzoic acid, decyl-4-carboxyphenylether, p-methylbenzoic acid, p-octylbenzoic acid, p-nonylbenzoic acid, p-bromobenzoic acid, p-chlorobenzoic acid, phenylacetic acid and the like.

In addition to the presence of the aliphatic or aromatic carboxylate moieties within the above-defined limits, the present improved process is necessarily conducted with agitation which provides top-to-bottom mixing throughout essentially the total volume of the reaction mass. This type of agitation, in addition to providing effective heat transfer throughout the entire reaction mixture, also serves to reduce foaming within the reaction and provides a means for conveniently discharging the solid highly crosslinked residues formed during the depolymerization as a result of chain-growth reactions occurring between partially depolymerized and thermally decomposed polymer fragments from the reaction without completely shutting down the reaction. Be essentially total volume mixing is meant that there are no "hot spots" within the reaction mixture so that highly efficient heat transfer within the reaction mass which contains solid polymeric residue dispersed therein is obtained and undesirable thermal degradation is minimized.

The specific equipment employed for the conduct of this process can vary and, in general, any means capable of achieving the prescribed mixing can be employed. A particularly useful means of agitation which provides top-to-bottom mixing and a highly efficient dividing-recombining action throughout essentially the entire volume of the mass are inverted multiple-blade conical vessels wherein the blades have a helical ribbon configuration and are arranged to rotate throughout essentially the entire mass and in close proximity to the interior surface of the bowl and in the direction which provides a downward flow within the reaction mass. Such equipment is known to the art and typical mixers and reactors of this type are described in U.S. Pat. Nos. 3,226,097, 3,314,660, and 3,352,543. The blades can be on a single shaft or mounted on separate shafts and they can be rotated in different directions and/or at different speeds and the pitch varied. When the blades are on a single shaft, the outer blade will trace an envelope essentially conforming to the interior shape of the reactor bowl while the interior helical blade(s) trace an envelope from and within the outer envelope and throughout the remainder of the reaction mass.

Reactors having two conical, helical ribbon blades which fit the inner contour of the bowl formed by two inverted intersecting vertical cones and whose axes coincide with the cone axes of the bowls and which intermesh as they rotate at the same speed in opposite directions are particularly useful for the conduct of the present improved depolymerization process and form a preferred embodiment thereof. With this type of equipment it is possible to adjust the blade-to-blade and blade-to-wall clearance by retracting each blade along its axis so that highly efficient mixing is obtained within the viscous plastic mass thereby obtaining maximum heat transfer which optimizes depolymerization of the polyester and minimizes the formation of undesirable by-products resulting from thermal degradation. The blades can rotate at up to 200 rpm but usually will be operated at a speed of 5 to 60 rpm.

It has been found that the rate of depolymerization obtained by the process of this invention is considerably faster than obtained with heretofore known batch-type operations and higher yields are possible. Mixing of the reaction mass and the corresponding improvement of the heat transfer characteristics of the reaction mass are possible only by using the above-defined agitation in the presence of the specified amount of monocarboxylate. When the monocarboxylate moieties are not present or are below the minimum concentration required, the agitation is ineffective and a solid mass is formed within the reaction which is impossible to agitate or if agitation does continue the mass "climbs up" the agitator so that efficient heat transfer is not possible.

Macrocyclic compounds obtained by the present process are primarily useful in applications where fragrance materials are employed. For example, the products of this process have utility in detergents (heavy duty and regular laundry), soaps (bar soaps, dish soaps and specialty beauty soaps), personal care products (both oils, shampoos, hair rinses, deodorants, shaving creams) and as fine fragrance components for perfumes, perfume oils, perfume fixatives, colognes, aftershave lotions and the like.

The following examples illustrate the invention more fully but are not intended to limit the scope thereof. In these examples, all parts and percentages are on a weight basis unless otherwise indicated.

EXAMPLE I

Poly(ethylene brassylate) was prepared by charging to a top-agitated resin kettle fitted with a distillation head and condenser 109 parts dimethyl brassylate containing approximately 2.3 mole percent methyl esters of monocarboxylic acids and 30.5 parts polymer grade ethylene glycol. A supported titanium catalyst (0.08 part), prepared from tetraisopropyl titanate and a naturally acidic montmorillonite clay in accordance with the teachings of U.S. Pat. No. 4,032,550, was added to the reaction mixture under a positive pressure of nitrogen and heating begun. When the temperature of the reaction mixture reached about 180° C. methanol began distilling from the reaction mixture and was collected. After most of the methanol was removed and the temperature increased to about 195° C.–205° C., a vacuum of 2 in. Hg was applied and increased slowly to 30 in. Hg. Samples were periodically removed from the reaction mixture for analysis and after about 11 hours the reaction mixture had an acid value of 0.1 and hydroxyl value of 15.3. Heating was terminated at this point, the reaction mixture cooled to about 180° C. and the vacuum broken with nitrogen. The high molecular weight poly(ethylene brassylate), viscosity of 177 centistokes at 210° C., was filtered to remove the supported titanium catalyst.

After dissolving 1.36 weight percent lead stearate into the above-prepared product, it was transferred to a stainless steel tank and maintained at 120° C. with agitation. From this tank the product was metered into an electrically heated two gallon stainless steel inverted vertical cone reactor fitted with two conical, helicoidal blades whose axes coincide with the cone axes of the bowl and which intermesh as they rotate in opposite directions to provide top-to-bottom mixing throughout the total volume of the reacton mixture. The blades are positioned within the reactor so that the maximum blade-to-wall clearance (distance between the blades and the interior surface of the reactor) is about 0.25" and the blades are driven with a high torque motor at about 20 rpm. A vacuum of about 1–2 mm Hg is maintained throughout the reaction. The rate of addition of poly(ethylene brassylate) was approximately four pounds per hour for the first two hours after which time the rate was ajusted to 1.5 pounds per hour and the addition continued for another 4½ hours. Ethylene brassylate was continuously distilled from the reactor and collected. The rate of ethylene brassylate recovery was essentially constant after about 1½ hours and was maintained for about 12 hours after which time it slowly decreased as the amount of poly(ethylene brassylate) in the reactor was depleted. After about 18 hours (total reaction time), at which time ethylene brassylate was being collected at a rate of only 0.25 pound per hour or less, the reaction temperature was reduced, the vacuum broken with nitrogen and the valve at the bottom of the reaction opened to discharge the solid residue present in the reactor. The brownish grandular material, believed to be crosslinked polyester, was extruded through the orifice by the action of the blades. When no further material could be extruded the port was closed, the temperature and pressure adjusted to within the operating range and the charging and entire cycle repeated in the manner described above. The depolymerization reaction was repeated in this semi-continuous manner through three complete cycles without encountering processing difficulties and without significantly affecting the rate of reaction or conversion. Conversions ranged from about 70 to 80% based on the weight of the poly(ethylene brassylate).

EXAMPLE II

In a manner similar to that described for Example I, 75 parts dimethyl brassylate and 38 parts ethylene glycol were reacted in the presence of 0.1 part stannous oxalate. The reaction mixture was heated for about 5½ hours at 160° to 185° C. under a nitrogen atmosphere with methanol distilling from the reaction mixture. A vacuum was applied and the reaction continued with the concurrent distillation of ethylene glycol for an additional 3½ hours. Additional stannous oxalate (0.4 part) was added with 0.82 part ethylene glycol distearate and the reaction continued for 6 hours at a temperature of about 185°–210° C. and pressure of 1 in. Hg. At the completion of the reaction period the tin content was increased by the addition of additional stannous oxalate. An amount of ethylene glycol distearate about comparable to the initial amount charged was also added and the mixture agitated at 185° C. under nitrogen for about one hour. The resulting polyester product containing 0.3 mole percent tin catalyst was depolymerized following the semi-continuous procedure already described and operating on twenty-four hour cycles. The temperature was maintained at about 290° C.–300° C. at 0.3 and 0.6 mm Hg while agitating the reaction mass at a rate of 20–30 rpm. The average feed rate was about 2.2 pounds/hour and the average rate of recovery of ethylene brassylate was 0.89 pound/hour with a maximum rate of 1.72 lbs/hour. At the end of the cycle period the granular powder was extruded from the reactor, vacuum reapplied to the system while increasing the temperature to within the operating range and the process continued.

When the equipment is modified to permit the solid product formed during the depolymerization to be removed without disrupting the operating conditions within the reactor, the depolymerization can be carried out as a continuous operation. This is accomplished by attaching a suitable collection and discharging means to the bottom of the reactor so that as the granular product begins to build up within the reactor it can be isolated from the principal reaction zone without disrupting the operating conditions therein and removed. The solid material which is removed can be discarded or it can be fed from the primary reactor into another reactor or reaction zone where it is possible, as a result of design variations and/or different operating conditions, to further "cook down" the crosslinked polyester and thereby obtain still higher conversions of the poly(ethylene brassylate).

EXAMPLE III

Diethyleneglycol azelate was obtained by the depolymerization of poly(diethyleneglycol azelate) obtained by condensing diethylene glycol and azelaic acid using stannous stearate as the catalyst. The mole ratio of the respective reactants and catalyst was 1.0:0.67:0.027. The catalyst was added after about 7 hours reaction when the rate of water evolution slowed. The maximum pot temperature was about 200° C. and after addition of the catalyst the pressure was reduced to 0.6 mm Hg. The resulting polyester containing 0.64 weight percent Sn was depolymerized in much the same manner as described in Example I, that is, by continuously charging the polyester to the heated (270°–310° C.), agitated (30–40 rpm) reactor under reduced pressure (0.2–0.8 mm Hg) over a period of about nine hours while continuously removing diethyleneglycol azelate until the recovery rate dropped to an unacceptable level. i.e. significantly below the maximum recovery rate of 3.5 pounds per hour. At this point the solid crosslinked polymeric material formed in the reactor was discharged and the process repeated. The yield of diethylene glycol azelate obtained during the first polymerization cycle was 86.7%.

EXAMPLE IV

Ethylene dodecanedioate was prepared by the depolymerization of poly(ethylene dodecanedioate) containing 1.36 weight percent lead stearate and 1.8 mole percent ethylene distearate so that the total monocarboxylate concentration in the polyester was 3.5 mole percent. The reaction was conducted at a maximum temperature of 320° C. with a pressure of about 0.3–0.4 mm Hg while agitating the reaction mass at 20 rpm. The rate of recovery of ethylene dodecanedioate ranged from about 0.88 to 1.1 pounds per hour and the conversion of poly(ethylene dodecanedioate) to be the desired product was 53%.

EXAMPLE V

Pentadecanolide was prepared by depolymerizing a mixed polyester comprised predominantly of 15-hydroxypentadecanoic acid containing minor amounts of dibasic acids and some mono- and difunctional alcohols. The reaction mixture was agitated at 20 rpm and the reaction temperature maintained between about 295° C. and 320° C. at a pressure between 0.25 and 0.9 mm Hg. A conversion of 58% was obtained and the maximum rate of recovery of pentadecanolide was 1.0 pounds per hour. The cycle time for the depolymerization was about 18 hours and no difficulties were encountered during subsequent cycles.

EXAMPLE VI

Poly(ethylene brassylate) terminated with 2 mole percent decyl-4-carboxyphenylether and containing 0.5 mole percent lead (obtained from lead acetate) was metered from a heated, agitated feed tank into an electrically heated vertically cone reactor fitted with two conical helical blades whose axes coincide with the cone axes of the bowl and which intermesh as they rotate in opposite directions to provide highly efficient top-to-bottom mixing throughout the total volume of the reaction mass. Blades were positioned to provide 0.25" blade-to-wall clearance and operated at 20 rpm. A vacuum of about 1–2 mm Hg and temperature of 290°–320° C. was maintained. The feed rate was maintained at about 5 pounds per hour for two hours and thereafter at 1.6 pounds per hour. Ethylene brassylate was continuously distilled from the reactor and collected at a rate of about 1.1 pounds per hour. Sixty percent conversion, based on the poly(ethylene brassylate), was obtained.

EXAMPLE VII

Poly(ethylene brassylate) terminated with 2 mole percent benzoic acid and containing 0.5 mole percent lead was continuously depolymerized employing a procedure similar to that described in Example VI. The reactor was operated continuously for approximately 18 hours by feeding polyester into the reactor while removing the depolymerized cyclic ester product. Crude ethylene brassylate was obtained in about 60% yield. This product was subsequently distilled to obtain a high quality fragrance chemical having no offensive off-odors suitable for use in cosmetic formulations. By discharging the solid residue formed in the reaction vessel through a port located at the bottom of the reactor, the depolymerization reaction was continued through additional cycles.

We claim:

1. In a process for the production of heteromacrocyclic compounds selected from the group consisting of cyclic esters and lactones having 8 to 20 carbon atoms in the ring by depolymerization of a linear polyester and ring closure at an elevated temperature and reduced pressure and in the presence of a metal catalyst, the improvement comprising conducting the process as a continuous or semi-continuous operation in the presence of 0.75 to 10 mole percent monocarboxylate derived from an aromatic monocarboxylic acid having 7 to 30 carbon atoms and with agitation which provides top-to-bottom mixing throughout essentially the total volume of the reaction mass in an inverted multiple-blade conical vessel wherein the blades have a helical configuration and are arranged to rotate throughout essentially the entire reaction mass and in close proximity to the interior surface of said conical vessel and in a direction which provides a downward flow within the reaction mixture.

2. The process of claim 1 wherein the aromatic monocarboxylate is present at a concentration of 1.25 to 5.0 mole percent.

3. The process of claim 2 wherein said conical vessel is formed by two inverted intersecting vertical cones and is fitted with two conical helical ribbon blades, which fit the inner contour of the bowl formed by the cones and whose axes coincide with the axes of the cones, and which intermesh as they rotate in opposite directions at the same speed.

4. The process of claim 1 wherein the reaction temperature is between 200° C. and 400° C., the pressure is less than 50 mm Hg, from about 0.01 to 10 weight percent of an oxide, hydroxide, halide or carboxylate of an organic acid having from 2 to 30 carbon atoms of a Group IIIa, IVa, IVb, Va, VIIb or VIII metal is employed to catalyze the depolymerization and the heteromacrocyclic compounds is a cyclic ester or cyclic ether-ester corresponding to the formula

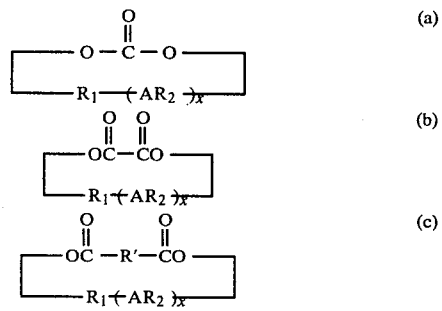

wherein R' is a bivalent hydrocarbon radical having 1 to 15 carbon atoms, $R_1$ is a saturated bivalent hydrocarbon radical having 1 to 17 carbon atoms, $R_2$ is a saturated bivalent hydrocarbon radical having 1 to 8 carbon atoms, A is oxygen or sulfur and x is an integer from 0 to 4, or a lactone or ether-lactone corresponding to the formula

wherein $R_1$ and x are the same as defined above, R" is a bivalent hydrocarbon radical having 1 to 18 carbon atoms and A is the same as defined above except that when x is zero A can only be oxygen.

5. The process of claim 4 wherein the catalyst is an oxide, hydroxide, chloride or carboxylate of a metal selected from the group consisting of magnesium, titanium, manganese, iron, cobalt, tin and lead and the cyclic ester or cyclic ether-ester corresponds to formula (c) where $R_1$ and $R_2$ are saturated bivalent hydrocarbon radicals having 2 to 13 carbon atoms, A and x are the same as defined above, R' is a bivalent hydrocarbon radical of the formula $-CR_3R_4-(CH_2)_y-$ where $R_3$ and $R_4$ are hydrogen or a $C_{1-4}$ alkyl group and y is an integer from 0 to 11, and the lactone or ether-lactone corresponds to formula (d) where $R_1$, A and x are the same as previously defined except that when x is zero A can only be oxygen, and R" is a bivalent hydrocarbon radical of the formula $-(CH_2)_u-CR_3R_4-$ where $R_3$ and $R_4$ are hydrogen or a $C_{1-4}$ alkyl group and u is an integer from 5 to 14.

6. The process of claim 5 wherein the reaction temperature is between about 250° C. and 350° C., pressure is in the range 0.01 to 10 mm Hg, from about 0.1 to 5 weight percent catalyst is used and the concentration of aromatic monocarboxylate ranges between 1.25 and 5 mole percent with the monocarboxylate having the general formula

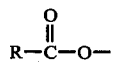

where the radical R is a phenyl or naphthyl which can be unsubstituted or substituted with one or more substituents selected from the group $C_{1-20}$ alkyl, $C_{3-8}$ cycloalkyl, $C_{1-20}$ alkoxy and halogen.

7. The process of claim 1 wherein the hetero-macrocyclic compound is a lactone or ether-lactone corresponding to formula

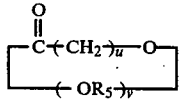

wherein $R_5$ is a saturated bivalent hydrocarbon radical having 2 to 13 carbon atoms, u is an integer from 5 to 14 and v is 0, 1 or 2 and conducted at a temperature between about 250° C. and 350° C., pressure in the range 0.01 to 10 mm Hg and in the presence of about 0.1 to 5 weight percent of an oxide, hydroxide, chloride or carboxylate of a metal selected from the group consisting of magnesium, titanium, manganese, iron, cobalt, tin and lead and 1.25 to 5 mole percent aromatic monocarboxylate having the general formula

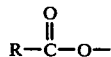

where the radical R is a phenyl or naphthyl which can be unsubstituted or substituted with one or more substituents selected from the group $C_{1-20}$ alkyl, $C_{3-8}$ cycloalkyl, $C_{1-20}$ alkoxy and halogen in an inverted multiple-blade conical vessel wherein the blades have a helical configuration and are arranged to rotate through essentially the entire reaction mass and in close proximity to the interior surface of said conical vessel and in a direction which provides a downward flow within the reaction mixture.

8. The process of claim 1 wherein the hetero-macrocyclic compound is a cyclic ester or cyclic ether-ester corresponding to the formula

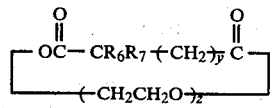

wherein $R_6$ and $R_7$ are hydrogen, methyl or ethyl groups, y is an integer from 0 to 11 and z is an integer from 1 to 4 and conducted at a temperature between about 250° C. and 350° C., pressure in the range 0.01 to 10 mm Hg and in the presence of about 0.1 to 5 weight percent of an oxide, hydroxide, chloride or carboxylate of a metal selected from the group consisting of magnesium, titanium, manganese, iron, cobalt, tin and lead and 1.25 to 5 mole percent aromatic monocarboxylate having the general formula

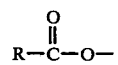

where the radical R is a phenyl or naphthyl which can be unsubstituted or substituted with one or more substituents selected from the group $C_{1-20}$ alkyl, $C_{3-8}$ cycloalkyl, $C_{1-20}$ alkoxy and halogen in an inverted multiple-blade conical vessel wherein the blades have a helical configuration and are arranged to rotate through essentially the entire reaction mass and in close proximity to the interior surface of said conical vessel and in a direction which provides a downward flow within the reaction mixture.

9. The process of claim 1 wherein the hetero-macrocyclic compound is a cyclic ester or cyclic ether-ester and corresponding to the formula

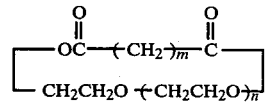

wherein m is an integer from 4 to 11 and n is 0 or 1 and conducted at a temperature between about 250° C. and 350° C., pressure in the range 0.01 to 10 mm Hg and in the presence of about 0.1 to 5 weight percent of an oxide, hydroxide, chloride or carboxylate of a metal selected from the group consisting of magnesium, titanium, manganese, iron, cobalt, tin and lead and 1.25 to 5 mole percent aromatic monocarboxylic having the general formula

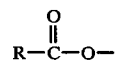

where the radical R is a phenyl or naphthyl which can be unsubstituted or substituted with one or more substituents selected from the group $C_{1-20}$ alkyl, $C_{3-8}$ cycloalkyl, $C_{1-20}$ alkoxy and halogen in an inverted multiple-blade conical vessel wherein the blades have a helical configuration and are arranged to rotate through essentially the entire reaction mass and in close proximity to the interior surface of said conical vessel and in a direction which provides a downward flow within the reaction mixture.

10. The process of claim 1 wherein the hetero-macrocyclic compound is ethylene brassylate and conducted at a temperature between about 250° C. and 350° C. pressure in the range 0.01 to 10 mm Hg and in the presence of about 0.1 to 5 weight percent of an oxide, hydroxide, chloride or carboxylate of a metal selected from the group consisting of magnesium, titanium, manganese, iron, cobalt, tin and lead and 1.25 to 5 mole percent aromatic monocarboxylate having the general formula

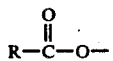

where the radical R is a phenyl or naphthyl which can be unsubstituted or substituted with one or more substituents selected from the group $C_{1-20}$ alkyl, $C_{3-8}$ cycloalkyl, $C_{1-20}$ alkoxy and halogen in an inverted multiple-blade conical vessel wherein the blades have a helical configuration and are arranged to rotate through essentially the entire reaction mass and in close proximity to the interior surface of said conical vessel and in a direction which provides a downward flow within the reaction mixture.

11. The process of claims 7, 8, 9 or 10 wherein the depolymerization is carried out in a conical vessel formed by two inverted intersecting vertical cones fitted with two conical helical ribbon blades, which fit the inner contour of the bowl formed by the cones and whose axes conicide with the axes of the cones, and which intermesh as they rotate in opposite directions at the same speed and the catalyst is an oxide, hydroxide, chloride or carboxylate of lead or tin.

12. The process of claim 11 wherein the catalyst is a lead carboxylate of an organic acid having from 8 to 22 carbon atoms.

* * * * *